(12) United States Patent
Reydel

(10) Patent No.: US 7,278,971 B2
(45) Date of Patent: Oct. 9, 2007

(54) ENDOSCOPIC MULTIPLE BIOPSY FORCEPS WITH SWING MEMBER

(75) Inventor: Boris Reydel, West Caldwell, NJ (US)

(73) Assignee: Inventio LLC, West Caldwell, NJ (US)

( * ) Notice: Subject to any disclaimer, the term of this patent is extended or adjusted under 35 U.S.C. 154(b) by 35 days.

(21) Appl. No.: 11/248,918

(22) Filed: Oct. 12, 2005

(65) Prior Publication Data

US 2006/0084886 A1    Apr. 20, 2006

Related U.S. Application Data

(60) Provisional application No. 60/618,514, filed on Oct. 14, 2004, provisional application No. 60/618,512, filed on Oct. 14, 2004.

(51) Int. Cl.
 *A61B 10/00* (2006.01)
 *A61B 17/00* (2006.01)
(52) U.S. Cl. ............... 600/564; 606/205; 606/208
(58) Field of Classification Search ........ 600/564–568; 606/205, 206, 208
See application file for complete search history.

(56) References Cited

U.S. PATENT DOCUMENTS 5,217,458 A * 6/1993 Parins ................... 605/48
7,105,000 B2 * 9/2006 McBrayer ............. 606/143

* cited by examiner

*Primary Examiner*—Max Hindenburg
*Assistant Examiner*—Jonathan Foreman
(74) *Attorney, Agent, or Firm*—Gary J. Gershik; Cooper & Dunham LLP

(57) ABSTRACT

A method and apparatus for mucosal biopsy including a stationary base clevis component, upon which an open frame jaw is actuated rotationally to engage tissue and retract samples. A rack and pinion mechanism drives the jaw motion, which can be controlled axially by the physician. A metal retriever component captures tissue from the open frame jaw, and advances the samples proximally into the collection chamber, where they are maintained as the retriever is returned to its most distal position. Furthermore, the open frame design employs a reliable and compact means for actuation that can be decoupled from sample transfer and storage functions.

16 Claims, 9 Drawing Sheets though Mondrowski cuts in a scissor-like fashion, Mondrowski suffers from the same shortcoming of the prior art discussed above. Specifically, Mondrowski has a limited range of motion that restricts the maneuverability of the biopsy forceps thereby complicating the removal of biopsy specimens at certain angles.

ENDOSCOPIC MULTIPLE BIOPSY FORCEPS WITH SWING MEMBER

REFERENCE TO RELATED APPLICATION

The present application is based on provisional application Ser. No. 60/618,512 filed Oct. 14, 2004 and provisional application Ser. No. 60/618,514 filed Oct. 14, 2004, the entire contents of which are herein incorporated by reference.

BACKGROUND

1. Technical Field

The present disclosure relates to biopsy forceps and, more specifically, to multiple biopsy forceps.

2. Description of the Related Art

Endoscopy is the practice of looking inside the body of a subject for medical purposes. In modern endoscopy, a small scope called an endoscope is inserted into the subject, often, but not necessarily, through a natural opening. The endoscope may incorporate a viewing device such as a camera or suitable optics for viewing the interior of the subject.

Examples of endoscopes include colonoscopes for examining the colon, gastroscopes for examining the stomach, and bronchoscopes for examining the bronchi.

Mucosal biopsies may be obtained to assess the histology of the gastrointestinal tract. Biopsy forceps may be used for the execution of mucosal biopsy. The mucosal biopsy tissue sample may be, for example from 2 mm to 4 mm in diameter.

Biopsy forceps may operate in conjunction with standard endoscopes and may be inserted through the working channel, engage the mucosa, and either cut or tear the sample from the surrounding tissue. Biopsy forceps may include means for removing and storing a biopsy sample. After the sample has been cut and stored, the biopsy forceps may be removed from the working channel and the specimen may be biopsied. In biopsy, samples may be stained, sliced and evaluated microscopically to evaluate the presence of disease, inflammation, and a host of other possible pathological responses.

When taking multiple biopsy samples, repeated insertion and removal of the biopsy forceps from the working channel may increase the risk of complications such as perforation and/or patient discomfort. Moreover, repeated insertion and removal may compromise both procedure time and the precision of the topography covered by the diagnostic procedure. It is therefore desirable to utilize biopsy forceps that have the ability to remove and store multiple biopsy specimens.

Traditional biopsy forceps may utilize a pair of jaws that may be made to simultaneously close around the biopsy specimen to cut and remove the specimen. These jaws have a limited range of motion that restricts the maneuverability of the biopsy forceps thereby complicating the removal of biopsy specimens at certain angles. It is therefore desirable to utilize biopsy forceps that have the ability to remove biopsy samples from greater angles.

One example of traditional biopsy forceps is German Patent Specification DE 43 19 968 C1, Mondrowski. Mondrowski relates to a biopsy forceps described as a tubular shaft instrument. Mondrowski utilizes a cutting jaw that appears capable of opening to an acute angle and cutting in a scissor-like fashion as the jaw closes. In Mondrowski, the jaw is attached to a toothed sector which engages with a toothed rack and the opening and closing of the jaw is achieved by actuating the toothed rack. Because Mond-

SUMMARY

An apparatus for excising tissue samples includes a flexible cylinder member for insertion into a working channel. The apparatus also includes a ridged cylinder member connected to the top of the flexible cylinder member. The apparatus also includes one or more guide channels running through the flexible cylinder member and the ridged cylinder member, the one or more guide channels guiding one or more pull wires. The apparatus also includes a hatch connected to the ridged cylinder member via a hinge such that the hatch may open to an angle up to 180 degrees of horizontal. The one or more pull wires attach to or wrap around the hatch such that actuation of the one or more pull wires closes the hatch.

An apparatus for excising tissue samples includes a stationary frame. The apparatus also includes a pinion casing with a pinion axel mounted on the stationary frame. The apparatus also includes a pinion rotatable mounted within the pinion casing and about the pinion axel. The apparatus also includes a swinging frame ridgedly connected to the pinion such that as the pinion rotates, the swinging frame swings between a proximal closed position and a distal open position. The apparatus also includes a rack interlocking with the pinion for causing the pinion to rotate. The apparatus also includes an actuator rod connected to the rack for actuating the rack and a pusher connected to the actuator rod or rack for pushing an excised tissue sample into a depository chamber. When the swinging frame is in the proximal closed position, the tissue sample may be excised and as the swinging frame is sent to the distal open position by rod actuation, the excised tissue sample is carried by the swinging frame to the distal side of the frame where it is pushed, by the pusher, into the depository chamber.

An apparatus for excising tissue samples includes a depository chamber for accommodating multiple tissue samples. The depository chamber has differential friction such that the degree of friction experienced by the excised tissue samples moving in a direction into the depository chamber is less than the degree of friction experienced by the excised tissue samples moving in a direction out of the depository chamber.

An apparatus for excising tissue samples includes a depository chamber for accommodating multiple tissue samples, the depository chamber includes negative pressure for sucking excised tissue samples into the depository chamber. The depository chamber also includes a slanted and perforated septum for keeping the excised tissue samples within a confined area within the depository chamber.

A method for excising a tissue sample from an excision site comprising the steps of cutting the tissue sample from the excision site using a blade attached to an open frame as the tissue sample protrudes from a hole in the open frame, and transporting the severed tissue from the excision site to a collecting chamber while the tissue sample rests on an outer surface of the open frame.

BRIEF DESCRIPTION OF THE DRAWINGS

A more complete appreciation of the present disclosure and many of the attendant advantages thereof will be readily obtained as the same becomes better understood by reference to the following detailed description when considered in connection with the accompanying drawings, wherein.

DETAILED DESCRIPTION

Figure 1A:
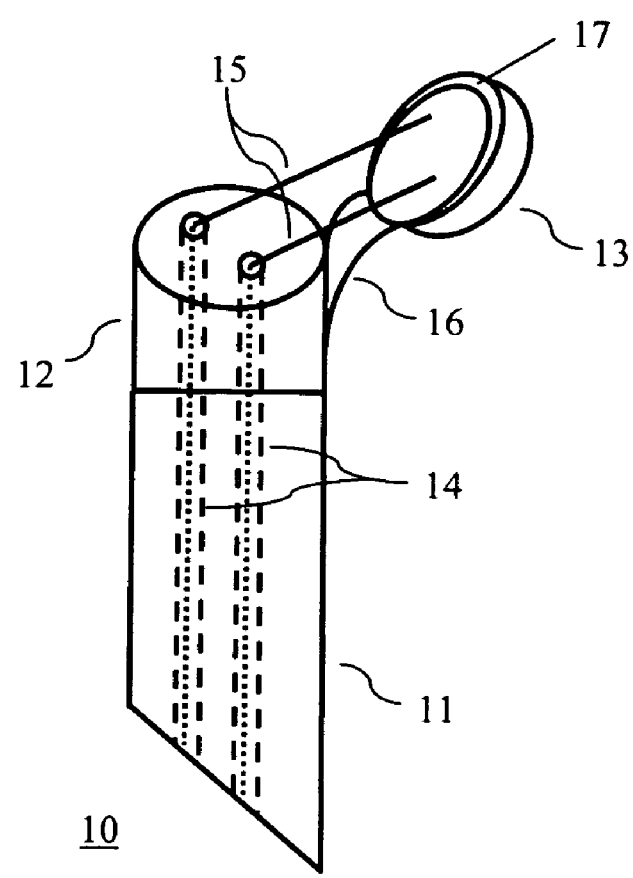
FIG. 1A is a diagram of a biopsy forceps according to one embodiment of the present invention.

An apparatus for excising tissue samples includes a flexible cylinder member for insertion into a working channel, a ridged cylinder member connected to the top of the flexible cylinder member, one or more guide channels running through the flexible cylinder member and the ridged cylinder member and a hatch connected to the ridged cylinder member via a hinge. The guide channels guides one or more pull wires. The hatch may open to an angle up to 180 degrees of horizontal. The pull wires attach to or wrap around the hatch such that actuation of the one or more pull wires closes the hatch.

The apparatus may additionally include a bladed or serrated cutting surface formed on the hatch and/or on the ridged cylinder end facing the hatch for facilitating the excision of the tissue sample.

A single guide channel may run through the flexible cylinder member and the ridged cylinder member. The single guide channel guides a single pull wire. The single pull wire runs through a guide channel in the hatch and connects to the ridged cylinder member. As the single pull wire is actuated, the hatch closes.

Two guide channels may run through the flexible cylinder member and the ridged cylinder member. The two guide channels guide two pull wires. The two pull wires connect to the hatch such that as the two pull wires are actuated, the hatch closes. The hinge may be spring loaded or comprised of a memory material that biases the hatch to the open position. The pull wires may have a memory shape bowing out at a segment between the hatch and a rim of the ridged cylinder member allowing for the excision of larger tissue samples. The top of the ridged cylinder member may be angled resulting in a larger opening for accommodating larger tissue samples. Excised tissue samples may be guided into a depository chamber within the ridged cylinder member by the closing of the hatch. The depository chamber may be able to accommodate multiple excised tissue samples.

An apparatus for excising tissue samples includes a stationary frame, a pinion casing with a pinion axel mounted on the stationary frame, a pinion rotatable mounted within the pinion casing and about the pinion axel, a swinging frame ridgedly connected to the pinion such that as the pinion rotates, the swinging frame swings between a proximal closed position and a distal open position. A rack interlocks with the pinion for causing the pinion to rotate. An actuator rod connected to the rack actuates the rack. A pusher connected to the actuator rod or rack pushes an excised tissue sample into a depository chamber. The tissue sample is excised when the swinging frame is sent to the proximal closed position. When the swinging frame is sent to the distal open position by rod actuation, the excised tissue sample is carried by the swinging frame to the distal side of the frame where it is pushed, by the pusher, into the depository chamber.

A bladed or serrated cutting surface may be formed on the proximal side of the frame for facilitating the excision of the tissue sample. A hole may be formed on the proximal side of the swinging frame such that as the swinging frame is sent to the closed position and the tissue sample is excised, the swinging frame closes against the stationary frame and the tissue sample is pushed through the hole in the swinging face so that as the swinging frame opens the tissue sample may be pushed by the swinging frame. The swinging frame may swing as much as 180 degrees as it moves between the proximal closed position and the distal open position. The depository chamber may be able to accommodate multiple excised tissue samples.

An apparatus for excising tissue samples includes a depository chamber for accommodating multiple tissue samples. The depository chamber has differential friction such that the degree of friction experienced by the excised tissue samples moving in a direction into the depository chamber is less than the degree of friction experienced by the excised tissue samples moving in a direction out of the depository chamber.

The apparatus may further include a flexible cylinder member for insertion into a working channel, a ridged cylinder member connected to the top of the flexible cylinder member, one or more guide channels running through the flexible cylinder member and the ridged cylinder member, the one or more guide channels guiding one or more pull wires, and a hatch connected to the ridged cylinder member via a hinge such that the hatch may open to an angle up to 180 degrees of horizontal. The pull wires attach to or wrap around the hatch such that actuation of the one or more pull wires closes the hatch thereby excising a tissue sample and moving the excised tissue sample into the depository chamber.

The apparatus for excising tissue samples may further include a stationary frame, a pinion casing with a pinion axel mounted on the stationary frame, a pinion rotatable mounted within the pinion casing and about the pinion axel, a swinging frame ridgedly connected to the pinion. As the pinion rotates, the swinging frame swings between a proximal closed position and a distal open position. The apparatus for excising tissue samples may further include a rack interlocking with the pinion for causing the pinion to rotate, an actuator rod connected to the rack for actuating the rack, and a pusher connected to the actuator rod or rack for pushing an excised tissue sample into the depository chamber. When the swinging frame is sent to the proximal closed position, the tissue sample may be excised and when the swinging frame is sent to the distal open position by rod actuation, the excised tissue sample is carried by the swinging frame to the distal side of the frame where it is pushed, by the pusher, into the depository chamber.

The inner surface of the depository chamber may be lined with one or more micro flaps. The micro flaps may be attached to a cord and the cord is mounted to the inside surface of the depository chamber. The micro flaps may be laser etched into the inside surface of the depository chamber. Tissue samples may be removed from the depository chamber by pushing the tissue samples through the depository chamber using a plunger.

An apparatus for excising tissue samples includes a depository chamber for accommodating multiple tissue samples. The depository chamber includes negative pressure for sucking excised tissue samples into the depository chamber and a slanted and perforated septum for keeping the excised tissue samples within a confined area within the depository chamber.

The apparatus may further include a flexible cylinder member for insertion into a working channel, a ridged cylinder member connected to the top of the flexible cylinder member, one or more guide channels running through the flexible cylinder member and the ridged cylinder member, the one or more guide channels guiding one or more pull wires, and a hatch connected to the ridged cylinder member via a hinge such that the hatch may open to an angle up to 180 degrees of horizontal. The pull wires attach to or wrap around the hatch such that actuation of the one or more pull wires closes the hatch thereby excising a tissue sample and moving the excised tissue sample into the depository chamber.

The apparatus for excising tissue samples may further include a stationary frame, a pinion casing with a pinion axel mounted on the stationary frame, a pinion rotatable mounted within the pinion casing and about the pinion axel, a swinging frame ridgedly connected to the pinion such that as the pinion rotates, the swinging frame swings between a proximal closed position and a distal open position, a rack interlocking with the pinion for causing the pinion to rotate, an actuator rod connected to the rack for actuating the rack, and a pusher connected to the actuator rod or rack for pushing an excised tissue sample into the depository chamber. When the swinging frame is sent to the proximal closed position, the tissue sample may be excised and when the swinging frame is sent to the distal open position by rod actuation, the excised tissue sample is carried by the swinging frame to the distal side of the frame where it is pushed, by the pusher, into the depository chamber.

The septum may be contoured. The septum may be convex. The septum may be concave. The septum may be planar. The planar septum may be angled between perpendicular and parallel to a central axis of the depository chamber in any direction. The planar septum may be angled 45 degrees from perpendicular to the central axis of the depository chamber in any direction.

A method for excising a tissue sample from an excision site includes cutting the tissue sample from the excision site using a blade attached to an open frame as the tissue sample protrudes from a hole in the open frame, and transporting the severed tissue from the excision site to a collecting chamber while the tissue sample rests on an outer surface of the open frame.

In describing the preferred embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner to achieve similar results.

FIG. 1A is a diagram of a biopsy forceps according to one embodiment of the present invention. The biopsy forceps 10 has a flexible cylinder section 11 which may be sufficiently long and flexible to be guided to the desired location within the subject's body. Connected to the flexible cylinder section 11 may be a ridged cylinder section 12. The ridged cylinder section 12 may provide structural stability useful to support the biopsy features. One or more guide channels 14, for example two guide channels 14, may be mounted within the ridged cylinder section 12 and the flexible cylinder section 11. Alternatively, the guide channels 14 may be mounted along the outside of the cylinder sections 11 and 12, or integrated into the wall of the cylinder sections 11 and 12. The guide channels 14 allow for the unimpeded movement of one or more, for example two, pull wires 15 within the guide channels 14. The pull wires 15 may be actuated either manually or with a powered actuator. The pull wires 15 may be used to draw in a hatch 13. The pull wires may be attached to the hatch 13 and/or a single pull wire may travel over the external surface of the hatch 13. When the pull wires are actuated, the hatch may close around the biopsy tissue. The hatch 13 may be a flat hatch or it may be cup-shaped. A hinge 16 may be used to connect the hatch 13 to the ridged cylinder section 12. The hinge 16 may be spring-loaded or may be constructed of a memory-material which may provide a bias for keeping the hinge 16 in the open position. A cutting surface 17 may be incorporated into the hatch 13 to facilitate the excision of the biopsy sample tissue. The cutting surface may be either bladed or serrated. The combination of the cutting surface and the closing of the hatch may accomplish the severing of the tissue.

Actuation of the pull wires 15 may be used to pull the hatch 13 completely closed and/or to position the hatch 13 and its cutting surface 17 to a desired angle to facilitate excision of the tissue. The novel design described above may allow for the hatch 13 to open as much as 180 degrees from the closed position. Because the hatch 13 may function as a cutting surface, the ability to open to either an acute, right or obtuse angle provides the forceps, according to embodiments of the present invention, the ability to more easily and more accurately excise tissue from a wide variety of approach vectors.

The pull wire may have a memory shape bowing out at the segment between the hatch and the rim of the ridged cylinder. This bowing out may allow for more tissue to be excised.

Figure 1B:
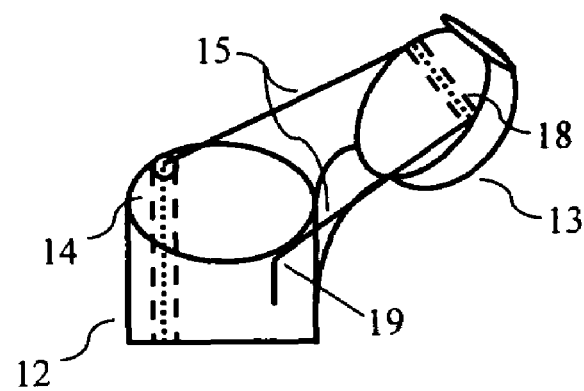
FIG. 1B is a diagram of a biopsy forceps according to embodiments of the present invention where only a single pull wire is used.

FIG. 1B is a diagram of a biopsy forceps according to embodiments of the present invention where only a single pull wire 15 is used. The wire may leave the guide channel 14 on the external surface of the ridged cylinder 12, just below its rim. The wire may then travel over the hatch through a short channel 18 made within the external surface of the hatch 13. The wire may then be connected to the ridged cylinder 12, for example, at a location 19 at the opposite point of the rim from where the guide channel 14 is located. In this way, a single pull wire may be used to actuate the hatch in a symmetric fashion.

As the hatch closes, the excised tissue may be pushed into the rigid cylinder. A flat hatch may be used to facilitate the pushing of the tissue into the cylinder.

Figure 1C:
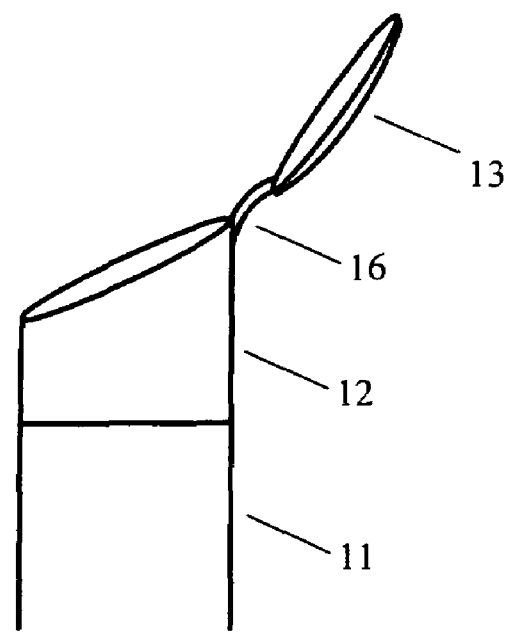
FIG. 1C is a diagram of a biopsy forceps according to embodiments of the present invention where the rim of the ridged cylinder slopes down at an angle.

FIG. 1C is a diagram of a biopsy forceps according to embodiments of the present invention where the rim of the ridged cylinder 12 slopes down at an angle, for example 45 degrees from horizontal. Such sloping may serve to increase the size of the opening of the ridged cylinder 12 so that larger tissue samples may be accommodated. In such embodiment, the hatch may swing inwards to a greater distance to meet flush with the rim of the ridged cylinder.

Figure 2:
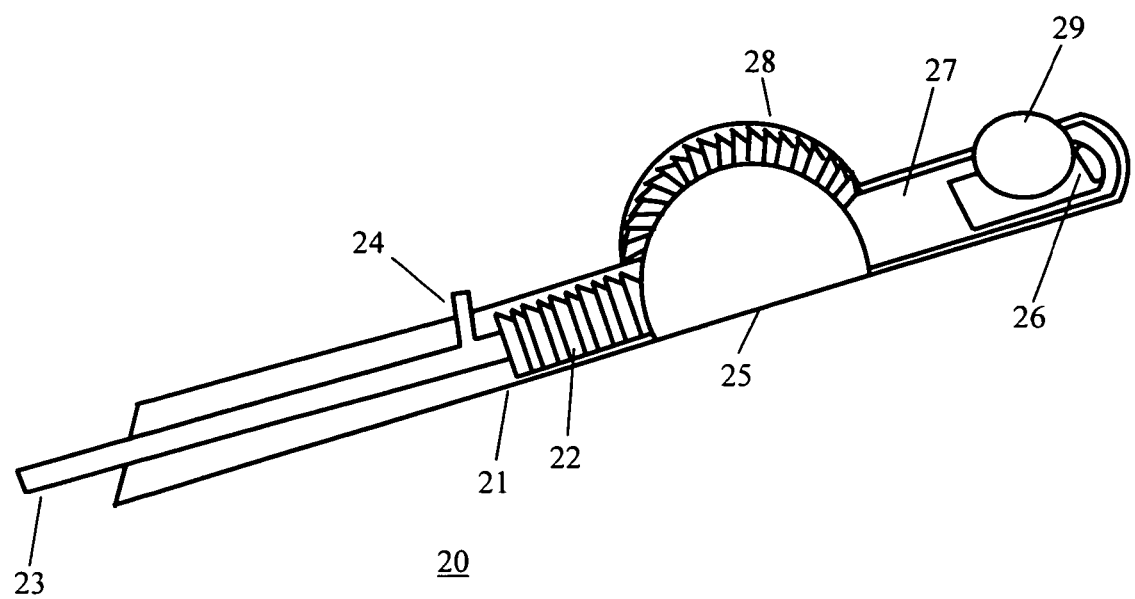
FIG. 2 is a diagram of a biopsy forceps according to embodiments of the present invention utilizing a rack and pinion pivot design.

Other embodiments of the present invention utilize a rack and pinion pivot design to excise and transfer a tissue sample into a depository chamber. FIG. 2 is a diagram of a biopsy forceps according to embodiments of the present invention utilizing a rack and pinion pivot design. The base of the biopsy forceps 20 is a base clevis component, anvil or stationary frame 21. On the stationary frame 21, for example on the center or proximally, is a pinion casing 25 having an axle (not shown). Within the pinion casing 25 is a pinion 28 that rotates about the axle. Attached to, and actuated by, the pinion 28 is a swinging frame 27 with a center hole. The swinging frame 27 may have a cutting element 26 that may be located on the tip of the swinging frame 27 and/or within the center hole of the swinging frame. The swinging frame 27 may contact the stationary frame 21 when the biopsy forceps is in the closed position, as shown in FIG. 2. In actuating the swinging frame 27 into the closed position, the cutting element 26 can be used to shave or cut the desired tissue sample 29. To facilitate this excision, the cutting element 26 may be bladed or serrated.

The cutting action may be achieved, for example, by the swinging frame 27 closing completely against the stationary frame, for example, with the cutting element 26 positioned on the front-underside of the swinging frame so that the tissue sample is severed in a cookie cutter style. Alternatively, or additionally, the cutting element 26 may be positioned within the center hole of the swinging frame, for example angled downwards and inwards, so that the biopsy forceps 20 may be pulled away from the excision site to complete the severance.

After the biopsy forceps in the closed position has been used to excise the desired tissue sample 29, the tissue sample 29 may be pushed through the opening in the swinging frame by the closing force so as to rest on the top of the swinging frame 27.

An actuator rod or rigid wire 23 may be attached to a rack 22. The rod 23 and rack 22 may sit on the stationary frame 21 and the rack 22 may interlock with the pinion 28 such that as the rod 23 is pushed forward, the pinion 28 rotates thereby rotating the swinging frame 27 about the pinion 28.

Figure 3:
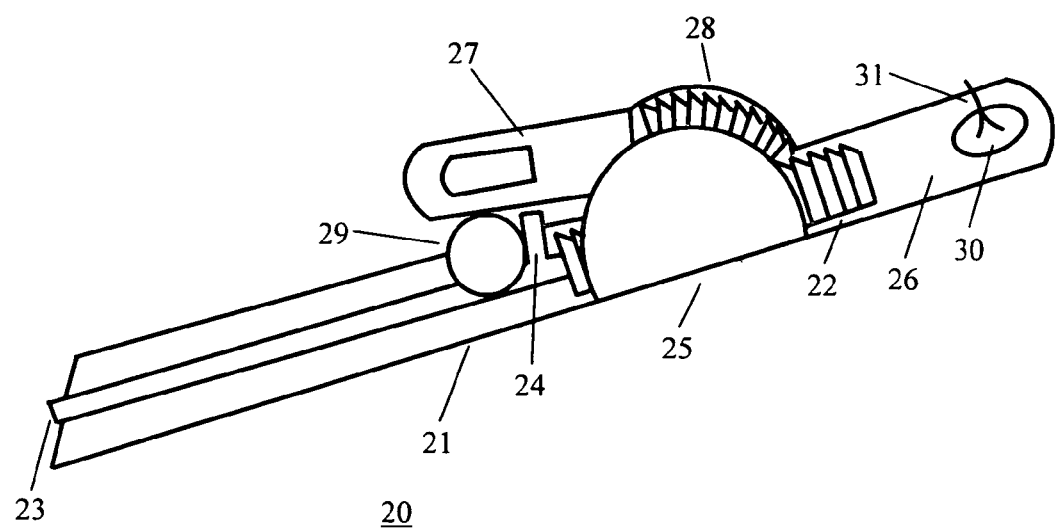
FIG. 3 is a diagram showing the biopsy forceps of FIG. 2, in the open position.

Due to the tackiness of the tissue sample 29, the tissue sample 29 may remain attached to the swinging frame 27 as it travels, up to 180 degrees from the closed position to the open position. FIG. 3 shows the biopsy forceps of FIG. 2 in the open position. In this state, the tissue sample 29 is moved to the rod 23. A pusher 24, for example a metal retriever component, attached to the rod 23 is placed such that it abuts the tissue sample 29 as it is brought down from the swinging frame 27.

FIG. 3 also shows a raised bump 30 and a curved spike 31. The raised bump 30 may be formed on the front portion of the stationary frame 21. The raised bump may be of any size or shape but should not be larger than the footprint of the hole in the swinging frame 27 as it rests in the closed position shown in FIGS. 2 and 4. The raised bump 30 may help to push the tissue sample upwards so that the tissue sample protrudes through the hole on the swinging frame 27 as the swinging frame closes to sever the tissue sample. Having the tissue sample protrude through the swinging frame may be useful to minimize the likelihood that the tissue sample does not properly disengages from the swinging frame as the tissue sample is pushed into a depository chamber as discussed below. Having the tissue sample protrude through the swinging frame may also be useful to provide leverage so that the tissue sample may be more easily severed, for example, by a blade positioned within the hole of the swinging frame as the biopsy forceps 20 is pulled away from the tissue excision site.

The curved spike 31 may be used in conjunction with the raised bump or in place of the raised bump. The curved spike may be uniformly thin and wire-like or it may widen at the base and form the bump 30. The curved spike 31 may be curved to match an arch traced by the tissue sample as it is carried from the excision site to the collecting chamber. Such a curvature will minimize resistance attributable to the spike as the tissue sample is lifted. The curved spike may minimize the chances of the tissue sample moving out of place as the sample excised and as the sample is pushed through the center hole of the swinging frame.

Figure 4:
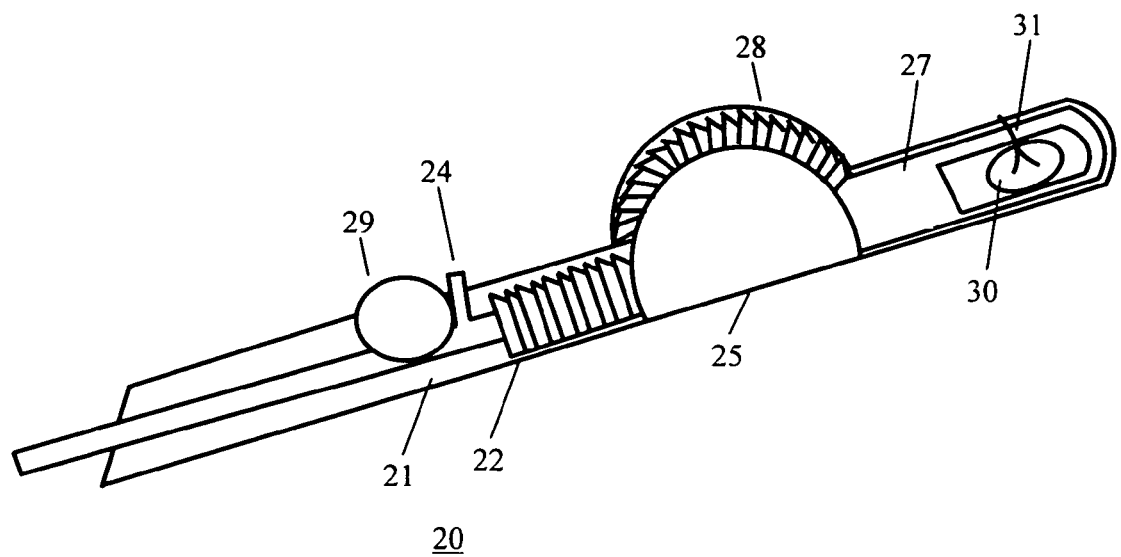
FIG. 4 is a diagram showing the biopsy forceps of FIGS. 2 and 3, returned to the closed position.

As the rod 23 is pulled back and the biopsy forceps 20 move back into the closed position to remove the next tissue sample, the pusher 24 pushes the tissue sample 29 off of the swinging frame 27 and into a depository chamber (not shown), such as a ridged cylinder, that may be placed on the frame 21. FIG. 4 shows the biopsy forceps of FIGS. 2 and 3 returned to the closed position.

Unlike the jaw of Mondrowski, whose mobility appears to be limited to acute angles, the swinging frame 27 of embodiments of the present invention may be open to any angle between 0 and 180 degrees of horizontal to initiate cutting of the tissue sample. Additionally, unlike Mondrowski where the sample must be cut in one direction and then pushed in the same direction for collection, embodiments of the present invention allow for the sample to be cut in one direction and then pushed in the opposite direction for collection. This approach allows for greater flexibility.

Although embodiment of the present invention may be of any size small enough to safely enter the working channel, according to some embodiments of the present invention, the outer diameter of the biopsy forceps may be 2.8 mm or 3.2 mm.

Endoscopic biopsy forceps according to embodiments of the present invention may be used to store multiple tissue samples in a depository chamber so that the endoscope does not need to be removed and reinserted.

According to one embodiment of the present invention, the depository chamber may employ a differential friction collecting chamber/catheter concept. According to this concept, there is greater friction in moving the sample out of the depository chamber than in pushing it in. Therefore, when a sample is pushed into the depository chamber, for example by using a pusher 24 as seen in FIG. 4, the sample may be easily pushed into the depository chamber but is unlikely to remain tacked to the pusher as the pusher pulls away.

Figure 5:
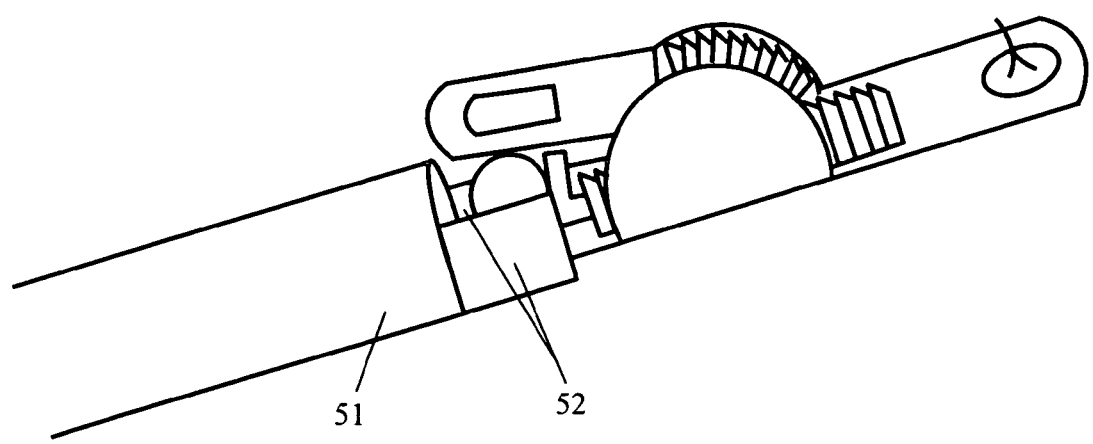
FIG. 5 is a diagram showing the biopsy forceps of FIGS. 2, 3 and 4 with a collecting chamber.

FIG. 5 is a diagram showing the biopsy forceps of FIGS. 2, 3 and 4 shown with a collecting chamber 51. The collecting chamber may be, for example, one of the collecting chambers shown in FIGS. 8 and 9 and described in detail below. The collecting chamber may be positioned such that it is as close to the tissue sample as possible without obstructing the motion of the swinging frame. By placing the collecting chamber close to the tissue sample, the risk of accidental loss of the tissue sample is minimized. Additionally, one or more side walls 52 may be used to further minimize the risk of loss of the tissue samples. The side walls may be formed as an integral unit with the collecting chamber and may be rectangular (as shown) or contoured to further minimize risk of loss. For example, the collecting chamber and side walls may be formed by removing a shaped section of the top of the collecting chamber just large enough to allow the swinging frame to come down unimpeded.

Figure 6A:
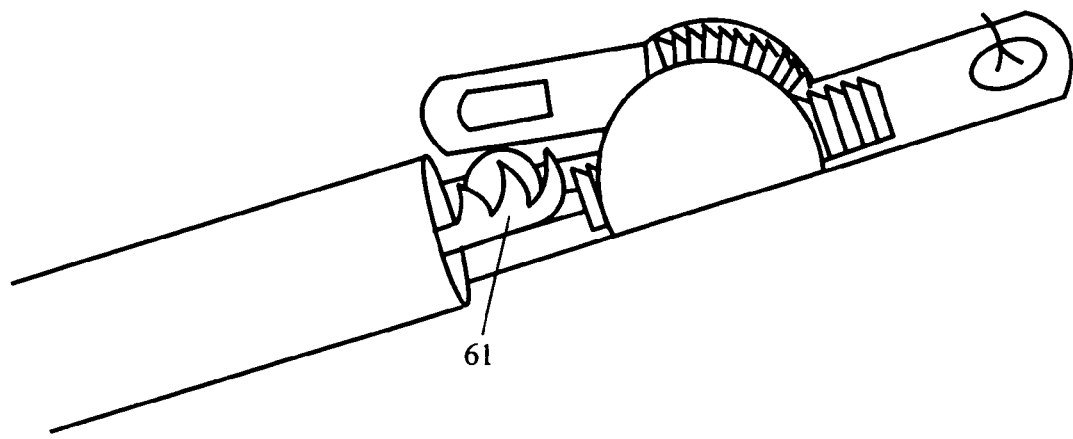
FIG. 6A is a diagram showing the biopsy forceps of FIGS. 2, 3, 4 and 5 with a pusher according to an alternative embodiment of the present invention.
Figure 6B:
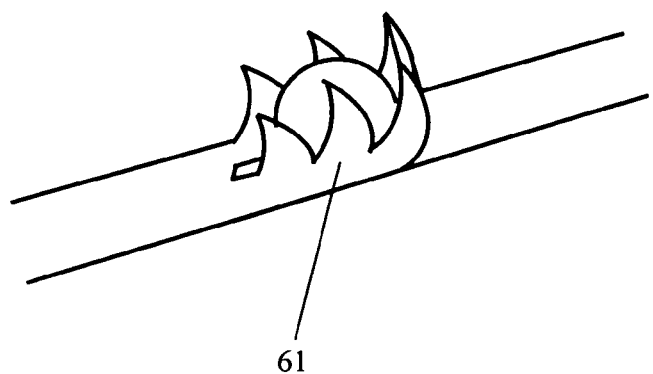
FIG. 6B is a close-up perspective view of the pusher of FIG. 6A.

The pusher 24 (FIG. 4) may alternatively comprise two or more posts or wires so that the tissue sample may be more pushed with greater stability. Alternatively, the pusher may be a pusher wall rather than a post or wire. The pusher should be able to push on the tissue sample but should not be positioned such that the tissue sample is impaled upon the pusher as the tissue sample is brought down by the swinging frame. To minimize the chances that an irregularly shaped tissue sample is accidentally impaled upon the pusher, the tip(s) of the pusher may be blunt, for example, rounded. According to one embodiment of the present invention, the pusher forms a pusher basket so that as the tissue sample is pushed, the chances of the tissue sample being lost are minimized. FIG. 6A is a diagram showing the pusher basket according to this embodiment of the present invention. The pusher basket 61 may comprise side structures to minimize the chances of the tissue sample being lost. FIG. 6B is a close-up perspective view of the basket pusher 61 shown in FIG. 6A.

Figure 7:
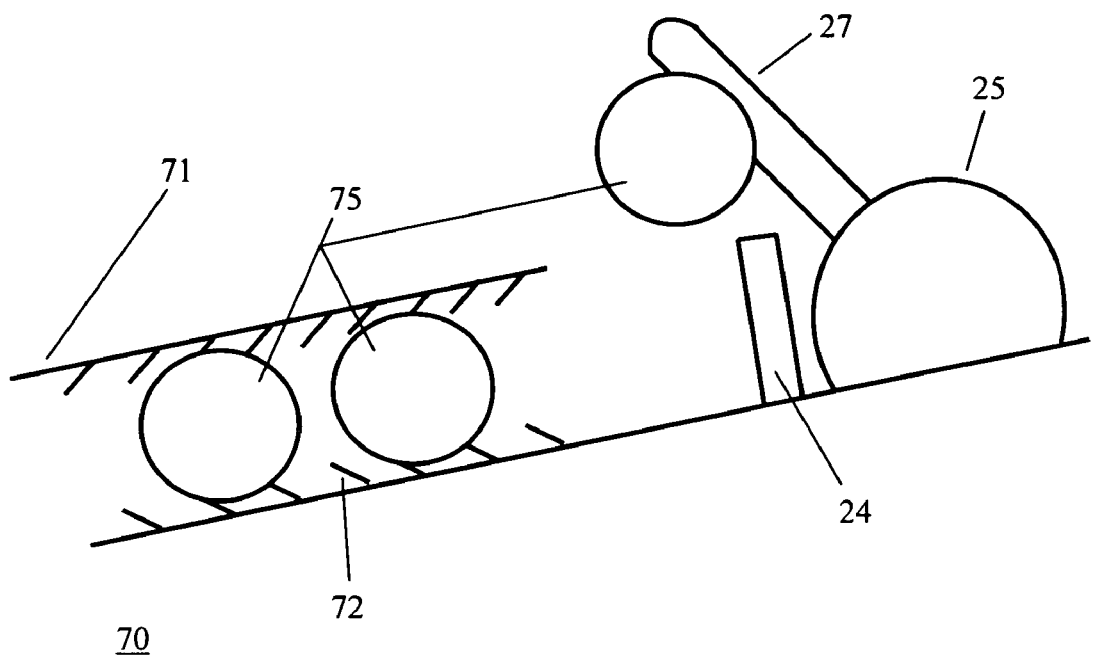
FIG. 7 is a diagram showing an example of a differential friction collecting chamber/catheter according to an embodiment of the present invention.

FIG. 7 is a diagram showing an example of a differential friction collecting chamber/catheter according to an embodiment of the present invention. According to this example 70, one or more micro flaps 72 may be positioned on the inside walls of the depository chamber 71. Then, as tissue samples 75 are pushed into the depository chamber 71, for example by a pusher 24, the samples 75 may easily move inwards. However, as the pusher 24 moves away, the micro flaps make it unlikely that a tissue sample 75 will remain tacked to the pusher 24 resulting in the loss of a tissue sample.

Many different techniques could be used to produce the micro flaps. For example, micro flaps may be attached to a fishing cord-like material that is then glued into the collecting chamber. Alternatively, laser etching techniques may be used. For example, the walls of the collecting chamber may be etched with a series of angled groves to produce the micro flap effect. Although the micro flaps shown in FIG. 7 appear as long wires, the micro flaps may be very small with respect to the diameter of the collecting chamber. The micro flaps need not be so large that they reduce the maximum size of a tissue sample that can easily be stored within the collecting chamber.

When the endoscope is removed, the samples may be freed from the depository chamber with the help of a plunger that can push the samples all the way through the endoscope. Alternatively, the depository chamber may form a detachable section of the endoscope, which can be separated to avoid pushing samples all the way through the endoscope. Alternatively, a side hole may be present in the collecting chamber for the removal of collected samples.

Figure 8:
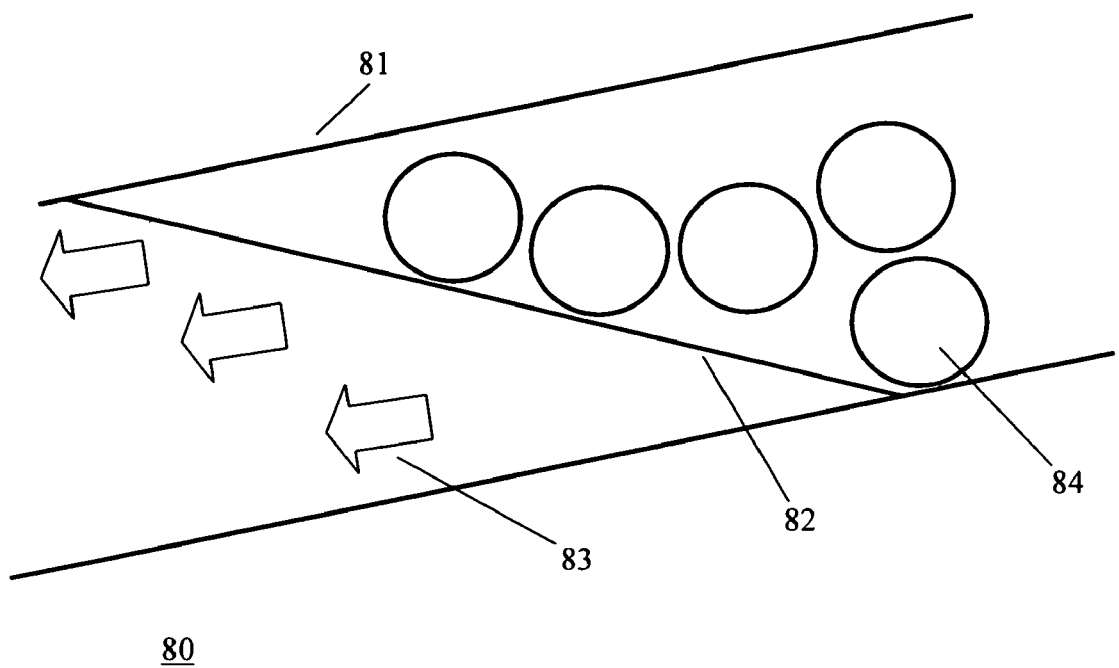
FIG. 8 is a diagram showing a depository chamber according to another embodiment of the present invention.

FIG. 8 is a diagram showing a depository chamber 80 according to another embodiment of the present invention. According to this embodiment, negative pressure (suction) 83 is provided to the chamber tube 81. A slanted and perforated septum 82 is positioned within the depository chamber tube 81. The septum 82 ensures collected tissue samples 84 stay confined within the depository chamber 80. By slanting the septum 8 2, the septum surface area can be increased thereby allowing for more samples to be collected and reducing the likelihood that the septum can become impacted with samples thereby blocking suction within the depository chamber.

Additionally, the slanted septum may allow the first samples to enter the chamber to roll to the "top" of the chamber (that area where the space between the septum and the chamber tube is the smallest). This may cause the suction to redistribute further down the septum to the unoccupied area.

The septum may be flat. Alternatively, the septum may be shaped. For example, the septum may be concaved forming a cone-shape or convex forming an inverted cone shape. The septum may have any number of perforations. For example, the septum may have 4 holes for accommodating 4 samples, or it may have a large number of holes for accommodating a large number of samples.

The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

What is claimed is:

1. An apparatus for excising tissue samples comprising:
   a flexible cylinder member for insertion into a working channel,
   a ridged cylinder member connected to the top of the flexible cylinder member;
   one or more guide channels running through the flexible cylinder member and the ridged cylinder member, the one or more guide channels guiding one or more pull wires; and
   a hatch connected to the ridged cylinder member via a hinge such that the hatch may open to an angle up to 180 degrees of horizontal,
   wherein the one or more pull wires attach to or wrap around the hatch such that actuation of the one or more pull wires closes the hatch, and
   wherein the one or more pull wires have a memory shape bowing out at a segment between the hatch and a rim of the ridged cylinder member allowing for the excision of larger tissue samples.

2. The apparatus of claim 1, additionally comprising a bladed or serrated cutting surface formed on the hatch and/or on the ridged cylinder end facing the hatch for facilitating the excision of the tissue sample.

3. The apparatus of claim 1, wherein a single guide channel runs through the flexible cylinder member and the ridged cylinder member, the single guide channel guiding a single pull wire, the single pull wire running through a guide channel in the hatch and connecting to the ridged cylinder member such that as the single pull wire is actuated, the hatch closes.

4. The apparatus of claim 1, wherein two guide channels run through the flexible cylinder member and the ridged cylinder member, the two guide channels guiding two pull wires, the two pull wires connected to the hatch such that as the two pull wires are actuated, the hatch closes.

5. The apparatus of claim 1, wherein the hinge is spring loaded or comprised of a memory material that biases the hatch to the open position.

6. The apparatus of claim 1, wherein the top of the ridged cylinder member is angled resulting in a larger opening for accommodating larger tissue samples.

7. The apparatus of claim 1, wherein excised tissue samples are guided into a depository chamber within the ridged cylinder member by the closing of the hatch.

8. The apparatus of claim 7, wherein the depository chamber can accommodate multiple excised tissue samples.

9. An apparatus for excising tissue samples comprising:
- a flexible cylinder member for insertion into a working channel,
- a ridged cylinder member connected to the top of the flexible cylinder member;
- one or more guide channels running through the flexible cylinder member and the ridged cylinder member, the one or more guide channels guiding one or more pull wires; and
- a hatch connected to the ridged cylinder member via a hinge such that the hatch may open to an angle up to 180 degrees of horizontal,
- wherein the one or more pull wires attach to or wrap around the hatch such that actuation of the one or more pull wires closes the hatch, and
- wherein the top of the ridged cylinder member is angled resulting in a larger opening for accommodating larger tissue samples.

10. The apparatus of claim 9, additionally comprising a bladed or serrated cutting surface formed on the hatch and/or on the ridged cylinder end facing the hatch for facilitating the excision of the tissue sample.

11. The apparatus of claim 9, wherein a single guide channel runs through the flexible cylinder member and the ridged cylinder member, the single guide channel guiding a single pull wire, the single pull wire running through a guide channel in the hatch and connecting to the ridged cylinder member such that as the single pull wire is actuated, the hatch closes.

12. The apparatus of claim 9, wherein two guide channels run through the flexible cylinder member and the ridged cylinder member, the two guide channels guiding two pull wires, the two pull wires connected to the hatch such that as the two pull wires are actuated, the hatch closes.

13. The apparatus of claim 9, wherein the hinge is spring loaded or comprised of a memory material that biases the hatch to the open position.

14. The apparatus of claim 9, wherein the one or more pull wires have a memory shape bowing out at a segment between the hatch and a rim of the ridged cylinder member allowing for the excision of larger tissue samples.

15. The apparatus of claim 9, wherein excised tissue samples are guided into a depository chamber within the ridged cylinder member by the closing of the hatch.

16. The apparatus of claim 15, wherein the depository chamber can accommodate multiple excised tissue samples.

* * * * *